(12) United States Patent
Stell (10) Patent No.: US 8,454,059 B2
(45) Date of Patent: Jun. 4, 2013

(54) CONNECTOR ASSEMBLIES, FLUID SYSTEMS INCLUDING CONNECTOR ASSEMBLIES, AND PROCEDURES FOR MAKING FLUID CONNECTIONS

(75) Inventor: Adrian Stell, Waterlooville (GB)

(73) Assignee: Pall Corporation, Port Washington, NY (US)

(*) Notice: Subject to any disclaimer, the term of this patent is extended or adjusted under 35 U.S.C. 154(b) by 0 days.

(21) Appl. No.: 12/880,405

(22) Filed: Sep. 13, 2010

(65) Prior Publication Data

US 2012/0061954 A1 Mar. 15, 2012

(51) Int. Cl.
*F16L 17/00* (2006.01)

(52) U.S. Cl.
USPC .......................... 285/377; 285/315

(58) Field of Classification Search
USPC ............... 285/377, 336, 401, 402, 361, 362, 285/396, 921, 315, 85, 86; 137/614.06; 251/89.5, 149.1, 149.9
See application file for complete search history.

(56) References Cited

U.S. PATENT DOCUMENTS

| | | | | |
|---|---|---|---|---|
| 2,887,124 A | * | 5/1959 | Mehl | 137/614.06 |
| 3,113,588 A | * | 12/1963 | Torres | 137/614.06 |
| 3,123,099 A | * | 3/1964 | Breuning et al. | 137/614.06 |
| 3,306,563 A | | 2/1967 | Soto | |
| 3,314,447 A | * | 4/1967 | Collar et al. | 137/614.06 |
| 3,685,795 A | | 8/1972 | Caster | |
| 3,706,318 A | * | 12/1972 | Baniadam et al. | 137/614.03 |
| 3,731,705 A | * | 5/1973 | Butler | 137/614.06 |
| 3,784,235 A | | 1/1974 | Kessler et al. | |
| 3,865,411 A | | 2/1975 | Rowe et al. | |
| 3,890,971 A | | 6/1975 | Leeson et al. | |
| 3,902,489 A | | 9/1975 | Carter | |
| 3,909,910 A | | 10/1975 | Rowe et al. | |
| 3,968,195 A | | 7/1976 | Bishop | |
| 3,986,508 A | | 10/1976 | Barrington | |
| 4,019,512 A | | 4/1977 | Tenczar | |
| 4,022,205 A | | 5/1977 | Tenczar | |
| 4,022,496 A | | 5/1977 | Crissy et al. | |
| 4,030,494 A | | 6/1977 | Tenczar | |
| 4,048,997 A | | 9/1977 | Raghavachari et al. | |
| 4,080,965 A | | 3/1978 | Phillips | |
| 4,149,534 A | | 4/1979 | Tenczar | |
| 4,161,949 A | | 7/1979 | Thanawalla | |
| 4,191,225 A | | 3/1980 | Ogle | |
| 4,195,632 A | | 4/1980 | Parker et al. | |
| 4,201,208 A | | 5/1980 | Cambio, Jr. | |
| 4,256,106 A | | 3/1981 | Shoor | |
| 4,265,280 A | | 5/1981 | Ammann et al. | |

(Continued)

FOREIGN PATENT DOCUMENTS

CH 677 964 A5 7/1991
DE 1 929 522 A1 12/1970

(Continued)

*Primary Examiner* — Aaron Dunwoody
(74) *Attorney, Agent, or Firm* — Leydig, Voit & Mayer, Ltd.

(57) ABSTRACT

A connector assembly has first and second connector bodies, a coupling mechanism arranged to couple the connector bodies at the first ends of the bodies, a moveable hollow piston, and a moveable actuator. The hollow piston moves from a first position to a second position in response to movement of the actuator from a first position to a second position. In the second position the hollow piston is sealed to the interiors of first and second connector bodies.

25 Claims, 6 Drawing Sheets

U.S. PATENT DOCUMENTS

| | | | |
|---|---|---|---|
| 4,289,337 A | 9/1981 | Roe | |
| 4,334,551 A | 6/1982 | Pfister | |
| 4,336,802 A | 6/1982 | Stone et al. | |
| 4,346,833 A | 8/1982 | Bernhardt | |
| 4,368,729 A | 1/1983 | Dossin | |
| 4,410,321 A | 10/1983 | Pearson et al. | |
| 4,418,945 A | 12/1983 | Kellog | |
| 4,432,755 A | 2/1984 | Pearson | |
| 4,443,215 A | 4/1984 | Smith | |
| 4,457,749 A | 7/1984 | Bellotti et al. | |
| 4,475,548 A | 10/1984 | Muto | |
| 4,488,961 A | 12/1984 | Spencer | |
| 4,507,119 A | 3/1985 | Spencer | |
| 4,508,367 A | 4/1985 | Oreopoulos et al. | |
| 4,511,359 A | 4/1985 | Vaillancourt | |
| 4,512,766 A | 4/1985 | Vaillancourt | |
| 4,516,971 A | 5/1985 | Spencer | |
| 4,521,263 A | 6/1985 | Benin et al. | |
| 4,531,768 A | 7/1985 | Summers | |
| 4,564,054 A | 1/1986 | Gustavsson | |
| 4,573,978 A | 3/1986 | Reilly | |
| 4,591,049 A | 5/1986 | Walter et al. | |
| 4,610,469 A | 9/1986 | Wolff-Mooij | |
| 4,610,670 A | 9/1986 | Spencer | |
| 4,617,012 A | 10/1986 | Vaillancourt | |
| 4,619,640 A | 10/1986 | Potolsky et al. | |
| 4,619,642 A | 10/1986 | Spencer | |
| 4,636,204 A | 1/1987 | Christopherson | |
| 4,680,025 A | 7/1987 | Kruger et al. | |
| 4,731,061 A | 3/1988 | Matkovich | |
| 4,737,214 A | 4/1988 | Leurink et al. | |
| 4,752,292 A | 6/1988 | Lopez et al. | |
| 4,753,697 A | 6/1988 | Shaposka et al. | |
| 4,767,400 A | 8/1988 | Miller et al. | |
| 4,768,568 A | 9/1988 | Fournier et al. | |
| 4,770,735 A | 9/1988 | Shaposka et al. | |
| 4,774,983 A * | 10/1988 | Abe | 137/614.2 |
| 4,792,163 A | 12/1988 | Kulle | |
| 4,793,880 A | 12/1988 | Shaposka et al. | |
| 4,798,605 A | 1/1989 | Steiner et al. | |
| 4,816,221 A | 3/1989 | Harvey et al. | |
| 4,828,557 A | 5/1989 | Persidsky | |
| 4,832,773 A | 5/1989 | Shaposka et al. | |
| 4,838,875 A | 6/1989 | Somor | |
| 4,840,690 A | 6/1989 | Melinyshyn et al. | |
| 4,843,017 A | 6/1989 | Oberhardt et al. | |
| 4,844,512 A | 7/1989 | Gahwiler | |
| 4,864,101 A | 9/1989 | Shaposka et al. | |
| 4,897,138 A | 1/1990 | Shaposka et al. | |
| 4,898,209 A | 2/1990 | Zbed | |
| 4,913,756 A | 4/1990 | Shaposka et al. | |
| 4,933,036 A | 6/1990 | Shaposka et al. | |
| 4,941,517 A | 7/1990 | Galloway | |
| 4,944,728 A | 7/1990 | Carrell et al. | |
| 4,950,260 A | 8/1990 | Bonaldo | |
| 4,978,446 A | 12/1990 | Lobdell | |
| 4,991,882 A | 2/1991 | Gähwiler | |
| 4,995,869 A | 2/1991 | McCarthy | |
| 4,998,713 A | 3/1991 | Vaillancourt | |
| 4,998,921 A | 3/1991 | Vickroy et al. | |
| 4,998,927 A | 3/1991 | Vaillancourt | |
| 5,017,259 A | 5/1991 | Kohsai | |
| 5,065,783 A | 11/1991 | Ogle, II | |
| 5,067,950 A | 11/1991 | Broadnax, Jr. | |
| 5,104,390 A | 4/1992 | Yum et al. | |
| 5,108,380 A | 4/1992 | Herlitze et al. | |
| 5,117,875 A | 6/1992 | Marrucchi | |
| 5,122,123 A | 6/1992 | Vaillancourt | |
| 5,122,129 A | 6/1992 | Olson et al. | |
| 5,158,549 A | 10/1992 | McCarthy | |
| 5,195,993 A | 3/1993 | Gianakos | |
| 5,224,936 A | 7/1993 | Gallagher | |
| 5,232,454 A | 8/1993 | Hollister | |
| 5,250,030 A | 10/1993 | Corsich | |
| 5,267,972 A | 12/1993 | Anderson | |
| 5,279,583 A | 1/1994 | Shober, Jr. et al. | |
| 5,279,591 A | 1/1994 | Simon | |
| 5,295,972 A | 3/1994 | Mischenko | |
| 5,334,180 A | 8/1994 | Adolf et al. | |
| 5,374,256 A | 12/1994 | Kriesel | |
| 5,380,049 A | 1/1995 | Smowton | |
| 5,393,101 A | 2/1995 | Matkovich | |
| 5,437,639 A | 8/1995 | Malenchek | |
| 5,439,258 A * | 8/1995 | Yates | 285/313 |
| 5,451,031 A * | 9/1995 | Purvis et al. | 251/89.5 |
| 5,483,993 A * | 1/1996 | Roebelen, Jr. | 137/614 |
| 5,492,147 A | 2/1996 | Challender et al. | |
| 5,549,568 A | 8/1996 | Shields | |
| 5,628,726 A | 5/1997 | Cotter | |
| 5,653,698 A | 8/1997 | Niedospial et al. | |
| 5,688,254 A | 11/1997 | Lopez et al. | |
| 5,738,671 A | 4/1998 | Niedospial, Jr. et al. | |
| 5,749,861 A | 5/1998 | Guala et al. | |
| 5,810,398 A | 9/1998 | Matkovich | |
| 5,839,715 A | 11/1998 | Leinsing | |
| 5,848,997 A | 12/1998 | Erskine et al. | |
| 5,868,433 A | 2/1999 | Matkovich | |
| 5,904,302 A * | 5/1999 | Brown | 239/586 |
| 5,989,240 A | 11/1999 | Strowe | |
| 6,009,901 A * | 1/2000 | Roberts | 137/614.06 |
| 6,155,294 A * | 12/2000 | Cornford et al. | 137/614 |
| 6,162,206 A | 12/2000 | Bindokas et al. | |
| 6,341,802 B1 | 1/2002 | Matkovich | |
| 6,394,992 B1 | 5/2002 | Sjöholm | |
| 6,408,880 B1 * | 6/2002 | Kaul | 137/614.06 |
| 6,453,945 B1 * | 9/2002 | Schumacher et al. | 137/614.06 |
| 6,517,526 B1 | 2/2003 | Tamari | |
| 6,880,801 B2 | 4/2005 | Matkovich et al. | |
| 7,090,191 B2 | 8/2006 | Matkovich et al. | |
| 7,350,535 B2 | 4/2008 | Liepold et al. | |
| 7,523,918 B2 | 4/2009 | Matkovich et al. | |
| 7,942,163 B2 * | 5/2011 | Sauer | 137/614.06 |
| 2007/0106264 A1 | 5/2007 | Proulx et al. | |
| 2007/0169825 A1 | 7/2007 | Packham et al. | |
| 2008/0128034 A1 * | 6/2008 | Fahl | 137/614.06 |

FOREIGN PATENT DOCUMENTS

| | | |
|---|---|---|
| DE | 32 10 964 A1 | 10/1983 |
| EP | 0 256 640 A2 | 2/1988 |
| EP | 0 545 598 A1 | 6/1993 |
| EP | 0 639 389 A1 | 8/1994 |
| EP | 2 060 835 A2 | 5/2009 |
| FR | 1 322 012 A | 2/1963 |
| FR | 1 380 396 A | 10/1964 |
| FR | 2 097 975 A5 | 3/1972 |
| FR | 2 606 643 A1 | 5/1988 |
| FR | 2 608 250 A1 | 6/1988 |
| FR | 2 614 386 A1 | 10/1988 |
| GB | 813284 A | 5/1959 |
| GB | 1 132 443 A | 10/1968 |
| GB | 2 008 705 A | 6/1979 |
| JP | 53-97293 A | 8/1978 |
| JP | 3-212276 A | 9/1991 |
| JP | U4-75542 A | 7/1992 |
| WO | WO 83/03538 A1 | 10/1983 |
| WO | WO 89/00432 A2 | 1/1989 |
| WO | WO 92/19314 A1 | 11/1992 |
| WO | WO 94/08173 A1 | 4/1994 |
| WO | WO 96/30076 A1 | 10/1996 |
| WO | WO 98/50105 A1 | 11/1998 |

* cited by examiner

CONNECTOR ASSEMBLIES, FLUID SYSTEMS INCLUDING CONNECTOR ASSEMBLIES, AND PROCEDURES FOR MAKING FLUID CONNECTIONS

FIELD OF THE INVENTION

The present invention is useful in many different industries, including the biopharmaceutical, biotechnology, food, beverage, cosmetic, and medical industries. In all of these industries, large or small systems of pipes, tubes, hoses and other conduits channel fluids from one location to another. The fluids may be gases, liquids, or mixtures of gases, liquids and/or solids. Many of these fluid systems, including biopharmaceutical and medical systems, transfer these fluids from one sterile location to another sterile location and have very strict requirements for sterility. The introduction into the fluid of unwanted contaminants, including biological contaminants, such as viruses or minute organisms, e.g., bacteria, and environmental contaminants, such as dust or dirt, can be highly detrimental for a great variety of reasons.

It is often necessary to make fluid connections in these systems, for example, to connect or disconnect existing conduits or components of the system, to install additional conduits for new fluid pathways, to add new components or replace existing components, or even to piece together an entirely new system. The present invention relates to connector assemblies and processes for making fluid connections. Connector assemblies and processes embodying the invention may include connector bodies and each connector body may have two ends. One end may be connected to a conduit or a component of the fluid system. The other end of the connector body may be coupled to the corresponding end of another connector body to make the fluid connection. Connector assemblies and processes embodying the invention allow this fluid connection to be made quickly and in a highly effective, reliable, and safe manner. Many embodiments further provide a sterile connection that resists the introduction of unwanted contaminants. Consequently, connector assemblies and processes embodying the invention are suitable for open, closed, and sterile closed fluid systems.

SUMMARY OF THE INVENTION

In accordance with one aspect of the invention, connector assemblies for making fluid connections may comprise first and second hollow connector bodies, a coupling mechanism, a hollow piston, and a moveable actuator. Each hollow connector body may include first and second ends, an exterior, and an interior which extends between the first and second ends. The coupling mechanism may be arranged to couple the first and second connector bodies at the first ends of the bodies. The hollow piston may also have first and second ends, an interior which extends between the first and second ends, an exterior, and first and second seals on the exterior of the piston. The piston may be moveable from a first position to a second position. In the first position, the piston may be positioned in the interior of the first connector body. In the second position, the piston may extend between the first and second connector bodies and the exterior of the piston may be sealed to the interiors of the first and second bodies. The actuator is also moveable from a first position to a second position. In the first position, the actuator may be located on the exterior of the first connector body. In the second position, the actuator may be located around the coupling mechanism. The actuator may be coupled to the piston to move the piston from the first position to the second position in response to movement of the actuator from the first position to the second position.

In accordance with another aspect of the invention, processes for making fluid connections may comprise coupling first and second hollow connector bodies at first ends of the bodies by a coupling mechanism. The processes may also comprise moving an actuator from a first position, wherein the actuator may be located on an exterior of the first connector body, to a second position, wherein the actuator may be located around the coupling mechanism. A hollow piston may be coupled to the actuator, and the processes may further comprise moving the hollow piston from a first position to a second position in response to movement of the actuator. In the first position the piston may be positioned in the interior of the first connector body, and in the second position the piston may extend between the first and second connector bodies and the exterior of the piston may be sealed to the interiors of the first and second bodies.

Devices and processes embodying these aspects of the invention provide many advantages. For example, by positioning the actuator around the coupling mechanism, the actuator surrounds and protects the coupled first ends and the coupling mechanism. This allows the connection provided by the coupling mechanism to be far more robust and tamper proof, preventing unintentional disassembly after actuation. In addition, by positioning the hollow piston between the first and second connector bodies and sealing the piston to the interiors of the connector bodies, the piston further reinforces the connection between the first and second bodies. This allows for the use of larger interiors in the connector bodies and piston, accommodating higher fluid flows through, and pressures within, the connector assembly.

In accordance with another aspect of the invention, connector assemblies for making fluid connections may comprise first and second hollow connector bodies, a coupling mechanism, a hollow piston, and a rotatable actuator. Each connector body may include first and second ends, an exterior, and an interior which extends between the first and second ends. The coupling mechanism may be arranged to couple the first and second connector bodies at the first ends of the bodies. The hollow piston may include first and second ends and an interior extending between the first and second ends. The piston may be moveable from a first position to a second position. In the first position, the piston may be slidably located in the interior of the first connector body and the first and second ends of the piston may be located between the first and second ends of the first connector body. In the second position, the piston may bridge the first and second connector bodies and seal against the interiors of the first and second bodies; the first end of the piston may be located between the first and second ends of the first connector body, and the second end of the piston may be located between the first and second ends of the second connector body; and the interior of the piston may fluidly communicate between the second ends of the first and second connector bodies. The rotatable actuator may be mounted around the exterior of at least one of the first and second connector bodies and may be coupled to the piston to move the piston from the first position to the second position in response to rotation of the actuator.

In accordance with another aspect of the invention, processes for making fluid connections may comprise coupling first and second hollow connector bodies at first ends of the bodies and rotating an actuator around an exterior of at least one of the first and second connector bodies. A hollow piston may be coupled to the actuator, and the processes may also comprise moving the hollow piston from a first position to a second position in response to rotating the actuator. In the first position, the piston may be slidably located in the interior of the first connector body and the first and second ends of the piston may be located between the first and second ends of the first connector body. In the second position, the piston may bridge the first and second connector bodies and seal against the interiors of the first and second bodies, the first end of the piston may be located between the first and second ends of the second connector body and the second end of the piston may be located between the first and second ends of the first connector body, and the interior of the piston may fluidly communicate between the second ends of the first and second connector bodies.

Devices and methods embodying these aspects of the invention also provide many advantages. For example, the piston may be contained within the first connector body in the first position and within the coupled connector bodies in the second position to mechanically isolate the piston from any tubing or piping that is connected to the connector assembly. Consequently, the connections to the tubing or piping will not be loosened when the piston is moved from the first position to the second position, and any harmful mechanical forces exerted on the connector assembly by the tubing or piping are not transferred to piston. Further, rotating or twisting the actuator to move the piston reduces the assembly forces, virtually eliminating the possibility that the components will be damaged when the piston is moved to the second position.

For some embodiments, the moveable actuator may be arranged not only to move the piston to the second position in response to movement of the actuator but also to maintain the piston in the second position. For example, the actuator may be locked in place once the piston is moved to the second position. Alternatively, further movement of the actuator after the piston is moved to the second position may uncouple the actuator from the piston, leaving the piston in the second position. In either event, accidental disconnection of the connector bodies is prevented, enhancing the reliability of the connection.

For some embodiments, the first ends of the first and second connector bodies may be covered by a seal layer. The seal layer may be arranged to be removed, for example, after the first ends of the connector bodies are coupled and before the piston is moved to the second position. This prevents contamination of the interiors of the first and second bodies and the piston and helps provide a sterile connection.

DETAILED DESCRIPTION OF EMBODIMENTS OF THE INVENTION

Figure 1:
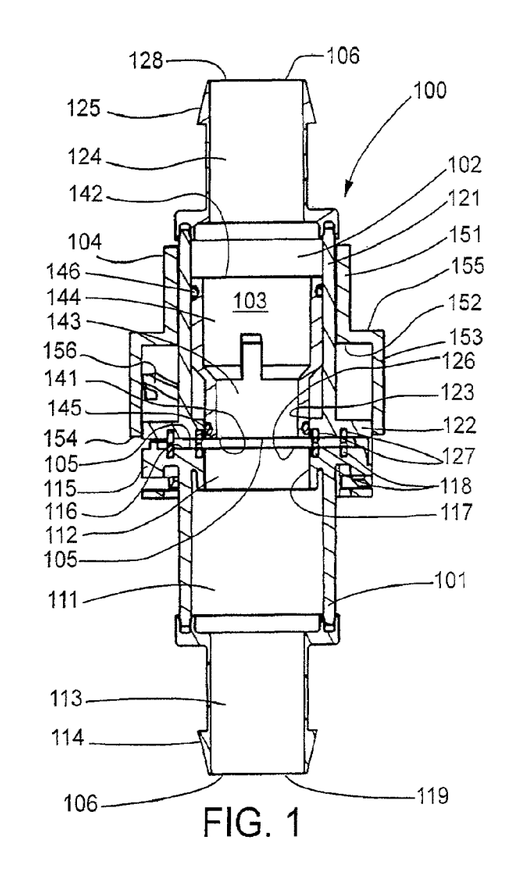
FIG. 1 is a cross sectional view of a connector assembly in an initial position.
Figure 2:
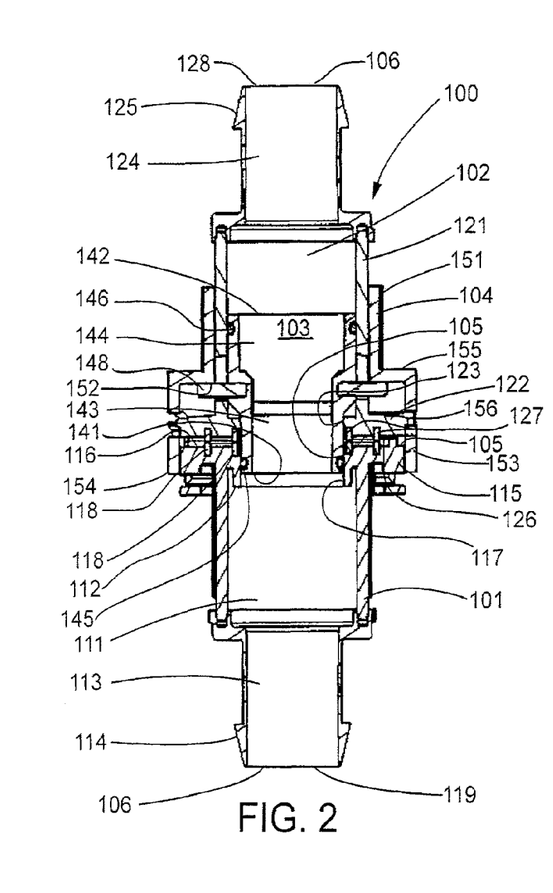
FIG. 2 is a cross sectional view of the connector assembly of FIG. 1 rotated by 90° and in an actuated position.

Connector assemblies embodying the invention may be configured in a wide variety of ways, and one of many different examples is shown in FIGS. 1 and 2. The exemplary connector assembly 100 may comprise female and male hollow connector bodies 101, 102, a moveable hollow piston 103, and a moveable actuator 104. Each connector body 101, 102 has first and second ends 105, 106, and the connector bodies 101, 102 may be coupled to one another at their first ends 105 by a coupling mechanism 107. All, or at least a portion, of the moveable piston 103 may initially be located in the interior of the male body 102. The moveable actuator 104 may be mounted on the exterior of at least one, or both, of the connector bodies 101, 102 and may be coupled to the moveable piston 103. In the illustrated embodiment, the actuator 104 may be moveably mounted to the male connector body 102 and may be coupled to the piston 103 through the male body 102. In response to movement of the actuator 104 from an initial position to an actuated position, the hollow piston 103 may move from an initial position to an engaged position, for example, as shown in FIGS. 1 and 2 respectively. In the engaged position, the hollow piston 103 may extend between or bridge the female and male bodies 101, 102 and may be sealed to the interiors of the female and male bodies 101, 102. The second ends 106 of the female and male bodies 101, 102 may be connected to a fluid system, for example, via hoses, pipes, or other conduits. Fluid may then flow through the connector assembly 100 via the second end 106 of either connector body 101, 102, into the interior of the connector body 101, 102, through the interior of the hollow piston 103 bridging the connector bodies 101, 102, and into the interior of the other connector body 102, 101, exiting the connector assembly 100 from the second end 106 of the other connector body 102, 101.

Figure 3:
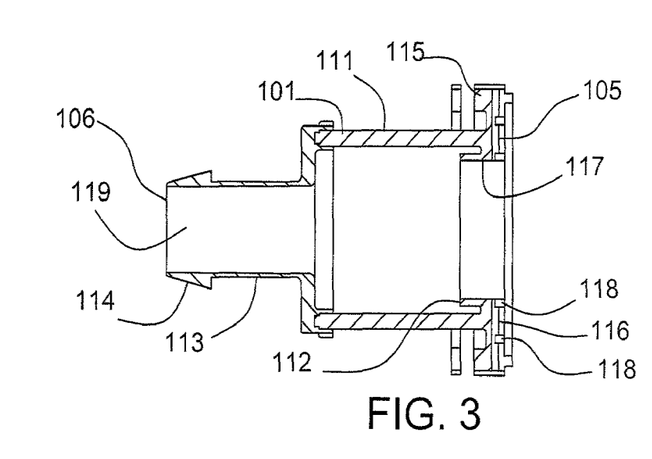
FIG. 3 is a cross sectional view of a female connector body.
Figure 4:
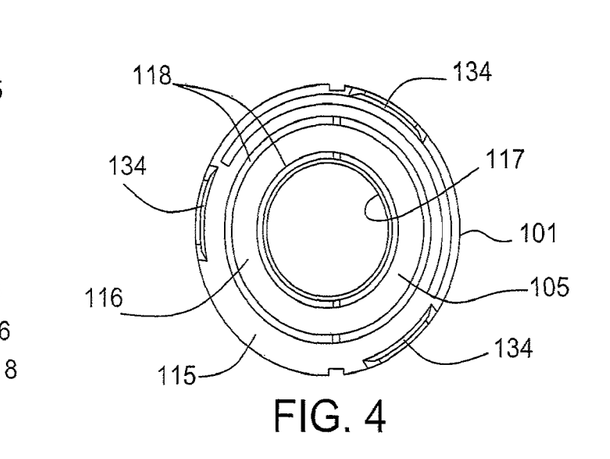
FIG. 4 is an end view of the female connector body of FIG. 3.

The female connector body, as well as the male connector body, may be configured in any of numerous ways to conduct fluid through the interior of the connector body and isolate the fluid from the external environment. Either connector body may be a single piece or a multipiece structure and may have any of various shapes. For example, in the embodiment illustrated in FIGS. 3 and 4, the female connector body 101 may comprise a multipiece structure having a hollow, generally cylindrical shape defining a fluid flow path through the interior of the female body 101 between the first and second ends 105, 106. Although the female body may have a uniform inner diameter between the first and second ends, the female body 101 shown in FIG. 3 has an inner diameter which varies along the axis of the body 101 between the first and second ends 105, 106. For example, the female body 101 may include a main barrel section 111 with a uniform inner diameter, a guide section 112 at the first end 105 with a uniform inner diameter smaller than the inner diameter of the barrel section 111, and a fitting section 113 which includes the second end 106 and also has a uniform inner diameter less than or about equal to the inner diameter of the barrel section 111. At the second end 106 of the female body 101, the fitting section 113 may include any of a wide variety of fittings for coupling the female body 101 to a hose, pipe, or other conduit of the fluid system. For example, the fitting 114 may be configured as the flange of a Triclover fitting or a hosebarb as shown in FIG. 3. At the first end 105 of the female body 101, a flange 115 may extend radially outwardly from the guide section 112 and/or the barrel section 111. The flange 115 may define a face 116, and the guide section 112 may open onto the face 116 at an opening 117 at the first end 105 of the female body 101. The face 116 of the flange 115 may be generally flat and may extend generally perpendicular to the axis of the female body 101. Any of numerous seals 118 may be provided on the face 116 of the flange 115, including, for example, gaskets, resilient sealing members, or O rings. In the illustrated embodiment, one or more seals 118 fashioned from a solidified resilient sealant may be formed on the face 116 of the flange 115. For example, two or more spaced, shallow concentric grooves may be formed in the face 115, and a resilient sealant, e.g., thermoplastic elastomer, may be overmolded in the grooves. The solidified sealant forms two spaced, concentric seals 118 that surround the opening 117 in the flange 115 and extend axially outwardly beyond the face 116 of the flange 115. The seals 118 may seal the face 116 of the female connector body 101 to the male connector body 102. The fluid flow path through the female connector body 101 may extend through the interior of the body 101 between the opening 117 in the flange 115 and an opening 119 in the fitting 114.

Figure 5:
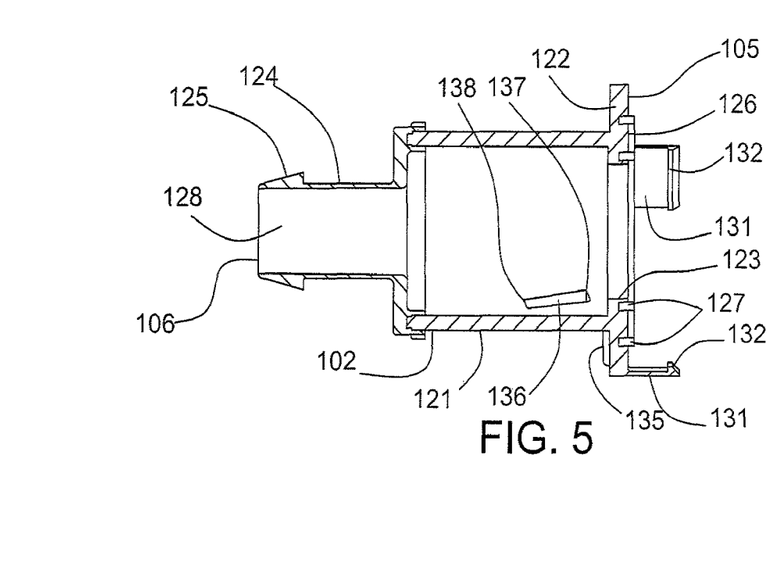
FIG. 5 is a cross sectional view of a male connector body.
Figure 6:
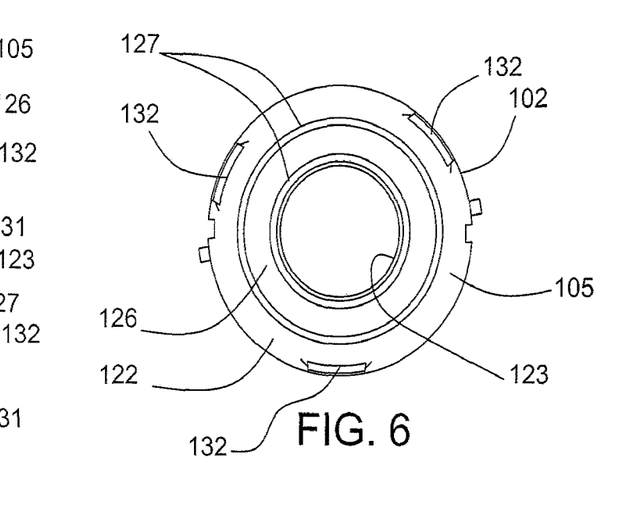
FIG. 6 is an end view of the male connector body of FIG. 5.

The male connector body 102 may also have a multipiece structure including a hollow, generally cylindrical shape defining a fluid flow path through the interior of the hollow body 102 between the first and second ends 105, 106, as shown in FIGS. 5 and 6. Although the male body may have a uniform inner diameter between the first and second ends, the illustrated male body 102 has an inner diameter which varies along the axis of the body 102 between the first and second ends 105, 106. For example, the male body 102 may include a main barrel section 121 with a uniform inner diameter, a flange 122 at the first end 105 with an opening 123 having a smaller uniform diameter than the inner diameter of the barrel section 121, and a fitting section 124 which includes the second end 106 and has a uniform inner diameter less than or about equal to the inner diameter of the barrel section 121. At the second end 106 of the male body 102, the fitting section 124 may include a fitting 125 for coupling the male body 102 to a hose, pipe, or other conduit of the fluid system. The fitting 125 of the male body 102 may be similar to or different from the fitting 114 of the female body 101. At the first end 105 of the male body 102, the flange 121 may define a face 126 and the face 126 may have one or more seals 127. The face 126, the seals 127, and the outer diameter of the flange 121 may be similar to those of the female connector body 101. Alternatively, the face of one of the connector bodies may have no grooves or seals and may serve as a seat for the seals on the face of the other connector body. The fluid flow path through the male connector body 102 may extend through the interior of the body 102 between the opening 123 in the flange 122 and an opening 128 in the fitting 114.

The male connector body and the female connector body may be coupled to one another in a wide variety of ways. For example, a mechanical coupling mechanism may be arranged to attach the male and female bodies with the interiors of the bodies being capable of fluidly communicating with one another. The coupling mechanism may be separate from or integral with the male and/or female bodies and may have any of numerous configurations. For example, the coupling mechanism may be a threaded assembly, a clamp assembly, or a ratchet assembly. In the illustrated embodiment, the coupling mechanism 107 may comprise a snap-fit assembly which may be variously implemented. For some embodiments, the snap-fit assembly may comprise a plurality of arms 131, catches 132, and ledges 133. The arms 131 may extend from one or both of the connector bodies, e.g., the male body 102, near the first end 105 of the body. Each arm 131 may have a catch 132 on the end of the arm 131, and the catches 132 grasp ledges 133 on one or both of the connector bodies, e.g., the female body 101, near the first end 105 of the body to hold the connector bodies 101, 102 together. In the illustrated embodiment three arms 131 extend axially from the outer edge of the flange 122 of the male body 102 and initially engage three generally axially oriented guide surfaces 134 on outer edge of the flange 115 of the female body 101 when the connector bodies 101, 102 are coupled. The arms 131 may bend outwardly slightly as they move along the guide surfaces 134 and then snap inwardly when the connector bodies 101, 102 are coupled, allowing the catches 132 to grasp the three ledges 133 at the end of the guide surfaces 134 on the back side of the flange 115 of the female body 101.

The male connector body may further include an arrangement for mechanically coupling the actuator to the male body while allowing movement, for example, rotational and/or axial movement, of the actuator with respect to the male connector body. The coupling arrangement may be configured in a great variety of ways. For example, the coupling arrangement may be configured as a pin-in-slot arrangement that allows both rotational and axial movement of the actuator on the male body. Although one or more pins may be associated with the actuator and one or more slots may be associated with the male body, in the illustrated embodiment the slot(s) may be associated with the actuator and the pin(s) may be associated with the male body. For example, as shown in FIGS. 5 and 6, one or more pins, e.g., two generally diametrically opposed pins 135, may extend radially outwardly from the male body 102. Although the pins 135 may be positioned at various locations along the male body 102, in the illustrated embodiment the pins 135 may be located near the first end 105 and may extend radially outwardly from the flange 122 and/or the barrel section 121. For example, the pins 135 may extend radially a short distance beyond the outer edge of the flange 122 and may be positioned in slots in the actuator.

In addition to being mechanically coupled to the moveable actuator, the male connector body may also allow the moveable actuator to be mechanically coupled to the moveable piston through the male body. For example, the male connector body may include openings through which the moveable actuator may be mechanically coupled to the moveable piston. In the illustrated embodiment the barrel section 121 may have one or more, e.g., two, elongated side openings 136. For example, the elongated openings 136 may be generally rectangular and have first and second ends 137, 138; may be located on diametrically opposite sides of the barrel section 121; and may begin at about the midpoint of the barrel section 121, extend axially or at an angle to the axis of the barrel section 121, and terminate prior to the flange 122. The side openings 136 allow the moveable actuator 104, which may be located on the exterior of the male body 102, to be mechanically coupled to the moveable piston 103, which may be located on the interior of the male body 102, through the barrel section 121.

The hollow piston may be configured in a variety of ways to move within the interior of the male connector body and/or the female connector body. For example, the piston may have a uniform inner diameter and/or a uniform outer diameter.

Figures 7, 8, 9, 10:
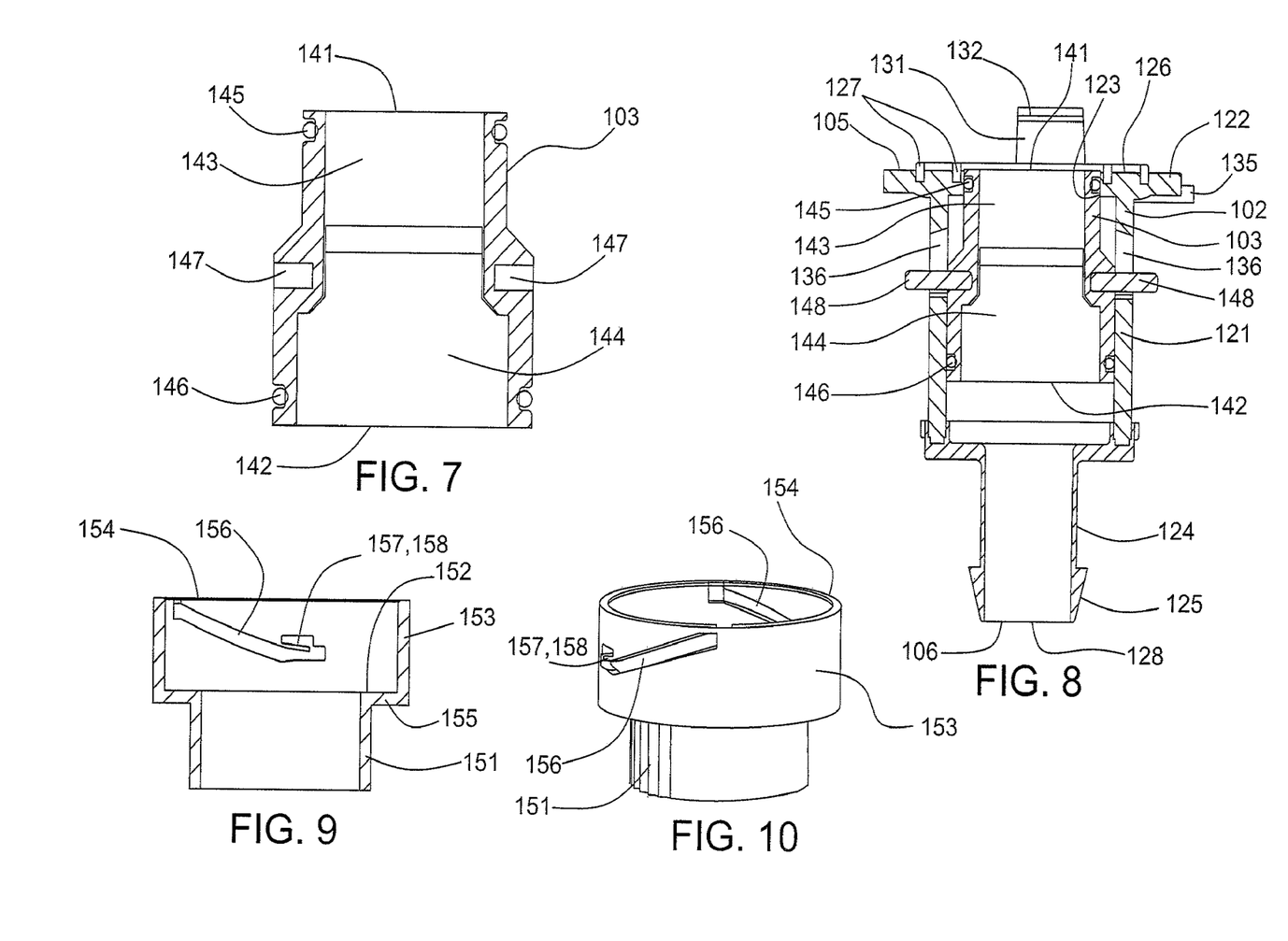
FIG. 7 is a cross sectional view of a hollow piston.
FIG. 8 is a cross sectional view of the hollow piston of FIG. 7 in the male connector body of FIG. 5.
FIG. 9 is a cross sectional view of a moveable actuator.
FIG. 10 is an isometric view of the moveable actuator of FIG. 9.

Alternatively, the inner diameter and/or the outer diameter of the piston may vary along the axis of the piston. Further, the outer diameter of the piston may correspond to the inner diameters of at least a portion of the male and/or female bodies. For example, as shown in FIGS. 7 and 8, the piston 103 may have first and second ends 141, 142, a smaller section 143 which includes the first end 141 of the piston 103, and a larger section 144 which includes the second end 142 of the piston 103. The outer diameter of the smaller section 143 may correspond to one or both of the diameter of the opening 123 in the flange 122 of the male connector body 102 and the inner diameter of the guide section 112 of the female connector body 101. The smaller section 143 may include a seal 145, for example, a shaft seal which extends around the outer circumference of the piston, such as an O ring contained in a groove. The seal 145 may be located near the first end 141 of the piston 103. When the piston 103 is in the engaged position, the seal 145 may seal the smaller section 143 of the piston 103 against the interior of the female connector body 101, for example, against the interior of the guide section 112 of the female body 101. For many embodiments, the seal 145 of the smaller section 143 of the piston 103 may also seal against the interior of the male connector body 102, for example, against the wall of the flange 122 which defines the opening 123 at the first end 105 of the male body 102, when the piston 103 is in the initial position. The outer diameter of the larger section 144 of the piston 103 may correspond to the inner diameter of the barrel section 121 of the male body 102. The larger section 144 may also include a seal 146, for example, a shaft seal which extends around the outer circumference of the piston, such as an O ring in a groove. The seal 146 may be located near the second end 142 of the piston 103. The seal 146 may seal the larger section 144 against the interior of the male connector body 102, for example, against the interior of the barrel section 121 of the male body 102 along the entire distance that the piston 103 moves from the initial position to the engaged position. Although the inner diameter of the larger section may be equal to the inner diameter of the smaller section, in the illustrated embodiment the inner diameter of the larger section 144 is larger than the inner diameter of the smaller section 143. For many embodiments the axial length of the piston 103 between the first and second ends 141, 142 may be less than the axial length of the male connector body 102 between the first and second ends 105, 106. For example, in the embodiment shown in FIGS. 7 and 8, the piston 103 may have an axial length which is less than or about equal to the axial distance from the first end 105 of the male body 102 to the end of the barrel section 111 that is connected to the fitting section 113. In the initial position, the piston 103 may then be completely contained within the male connector body 102.

The moveable piston and the moveable actuator may be mechanically coupled in any of numerous ways to allow at least axial movement, or axial and rotational movement, of the piston in response to axial and/or rotational movement of the actuator. For example, any of numerous mechanical couplings may be used to couple the piston and the actuator through the male connector body. In the illustrated embodiment, the outer surface of the piston 103 may include one or more, e.g., two, structures for coupling the moveable piston 103 to the moveable actuator 104 through the one or more side openings 136 in the male connector body 102. For example, the piston 103 may have two recesses 147 which open onto the outer surface but not the interior of the piston 103. The recesses 147 may be located between the seals 145, 146 on the piston 103 and may be positioned alongside of the side openings 136 in the male connector body 102. A protrusion, for example, a post 148, may be seated in each recess 147 and may extend generally radially through the corresponding side opening 136. The posts 148 may terminate beyond the outer surface of the male connector body 102 and may interact with the moveable actuator 104.

The moveable actuator may be configured in any of numerous ways to move the piston from an initial position, in which all or at least a portion of the piston is within the male connector body, to an engaged position, in which the piston bridges the male and female connector bodies. For example, as shown in FIGS. 9 and 10, the moveable actuator 104 may comprise a sleeve 151 mounted around the exterior of the male connector body 102, for example, around the barrel section 121. The sleeve 151 may have a first end 152 and an inner diameter that corresponds to the outer diameter of the male body 102, for example, the outer diameter of the barrel section 121. For many embodiments the moveable actuator may be mechanically coupled to the moveable piston without being integrally connected to the piston. For example, the sleeve 151 may be positioned on the exterior of the male connector body 102 with the piston posts 148 between the first end 105 of the male body 102 and the first end 152 of the sleeve 151. As the actuator 104 moves from its initial position to the actuated position, the first end 152 of the sleeve 151 contacts and moves the piston posts 148 along the side openings 136 in the male connector body 102. The piston posts 148, in turn, move the piston 103 from its initial position to the engaged position. If the side openings are oriented axially, the piston may move only axially within the male body. In the illustrated embodiment the side openings 136 may be oriented at an angle to the axis of the male body 102. As the posts 148 move along the angled side openings 136, a rotational movement in addition to an axial movement is imparted to the piston 103 by the posts 148. This rotational movement helps loosen the frictional engagement of the seals 145, 146 of the piston 103 against the interior of the male body 102, facilitating movement of the piston 103 from the initial position to the engaged position. From the actuated position, further movement of the actuator 104 toward the first end 105 of the male body 102 may be prevented, for example, because the piston posts 148 may contact the first ends 137 of the side openings 136 in the male body 102. Further, because the piston 103 is not integrally connected to the actuator 104, e.g., the piston posts 148 are not integrally connected to the sleeve 151, movement of the actuator 104 in the opposite direction uncouples the piston 103 from the actuator 104, e.g., breaks the contact between the piston posts 148 and the first end 152 of the sleeve 151, and leaves the piston 103 in the engaged position. Consequently, the actuator 104 may not be deactuated and the piston 103 may not be disengaged from the female connector body 101, making the connector assembly 100 a single use device. Alternatively, for other embodiments the piston may be integrally connected to the actuator, e.g., the piston posts may be fixed to the sleeve. The piston may then be moved back and forth between the initial and engaged positions in response to movement of the actuator back and forth between the initial and actuated positions.

Figure 11:
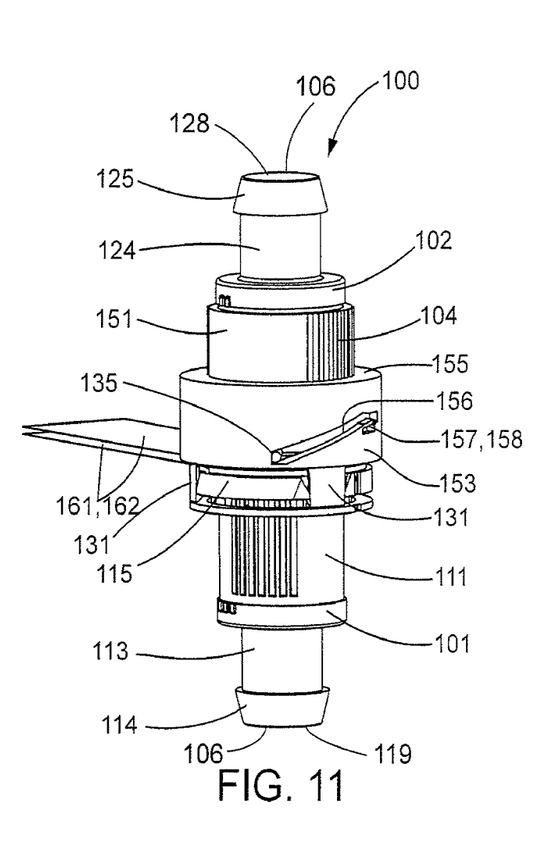
FIG. 11 is an isometric view of the connector assembly with the moveable actuator in the initial position.
Figure 12:
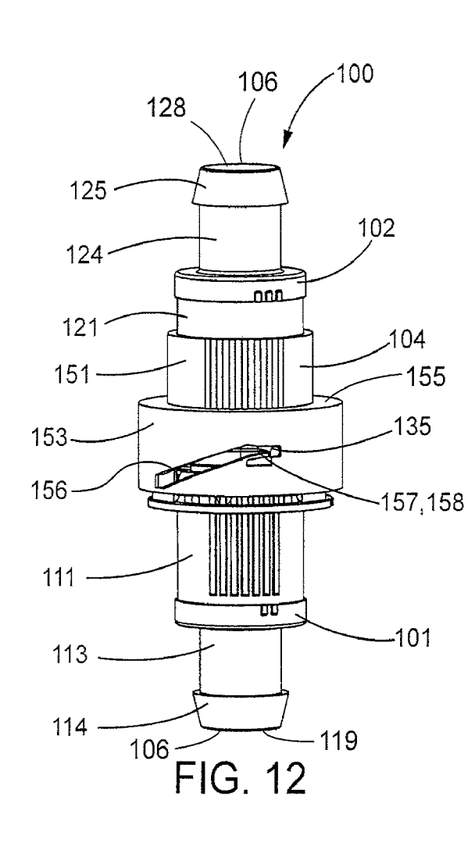
FIG. 12 is an isometric view of the connector assembly with the moveable actuator in the actuated position.

The movable actuator may also be configured in any of numerous ways to move to a position around the coupling mechanism at the first ends of the coupled male and female connector bodies, for example, to prevent disengagement of and/or tampering with the coupling mechanism. For example, the movable actuator 104 may comprise a collar 153 mounted around the exterior of the male connector body 102, for example, around the flange 122 and/or the barrel section 121. The inner diameter of the collar 153 may be approximately equal to or slightly larger than the outer diameters of the flanges 115, 122 of the female and male bodies 101, 102, the outer diameter at the exterior of the arms 131 of the coupling mechanism 107, and the outer diameter at the posts 148 of the piston 103. The collar 153 may be open at a first end 154 and may be fixedly connected to the sleeve 151 at the opposite end, for example, by a radially extending flange 155. In the initial position of the movable actuator 104, the first end 154 of the collar 153 may be positioned near the first end 105 of the male body 102 axially away from the arms 131 of the coupling mechanism 107, for example, around the outer edge of the flange 122 of the male body 102, as shown in FIG. 11. The arms 131 of the coupling mechanism 107 are then free to bend outwardly as they engage the guide surfaces 134 of the female body 101 when the connector bodies 101, 102 are coupled to one another. As the movable actuator 104 moves to the actuated position after the connector bodies 101, 102 are coupled, the collar 153 moves axially along the outer edges of the flanges 122, 115 and the exterior surfaces of the arms 131 of the coupling mechanism 107. As shown in FIG. 12, the collar 153 in the actuated position may extend over the exteriors of the coupled male and female bodies 102, 101 at the first ends 105. In the actuated position, the collar 153 may also extend over all or at least a significant portion of the arms 131 of the coupling mechanism 107 closely adjacent to the arms 131, preventing the arms 131 from bending outwardly and disengaging the catches 132 from the ledges 133 of the coupling mechanism 107.

The movable actuator may be arranged to move only axially between the initial position and the actuated position. However, for many embodiments, including the illustrated embodiment, the movable actuator 104 may be arranged to move both rotationally and axially from the initial position to the actuated position. For example, the slots 156 of the pin-in-slot arrangement coupling the movable actuator 104 to the male connector body 102 may extend at an angle to the axis of the connector body 102, e.g., may be helical. Each slot 156 may extend helically along the actuator 104, for example, along the collar 153, from an initial position of the slot 156 closer to the first end 105 of the male body 102 to an actuated position of the slot 156 further from the first end 105. The pins 135 extending from the male body 102 may be captured in the helical slots 156, and the pins 135 may be located in the initial position of the slots 156 when the actuator 104 is in its initial position on the male connector body 102. Once the female and male bodies 101, 102 are coupled at their first ends 105, the actuator 104 in its initial position may be rotated. Each pin 135 then moves relative to the helical slot 156 from the initial position toward the actuated position of the slot 156, driving the movable actuator 104 axially from its initial position toward the actuated position. At the actuated position of each helical slot 156, a locking mechanism 157 may lock the pin 135 in place. The locking mechanism 157 may be variously configured. For example, in the illustrated embodiment the locking mechanism 157 may comprise a biased clip 158. Each clip 158 may be arranged to bend out of the way as the pin 135 moves over the clip 158 toward the actuated position of the slot 156 and then spring back after the pin 135 clears the clip 158 in the actuated position of the slot 156, locking the pin 135 in the actuated position in the slot 156.

Figure 13:
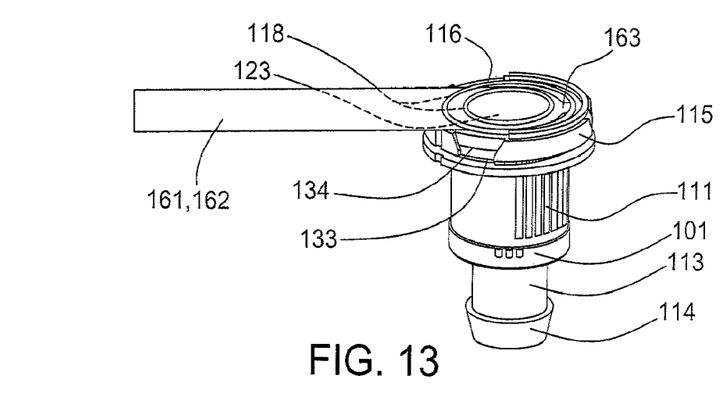
FIG. 13 is an isometric view of the female connector body and the seal layer.
Figure 14:
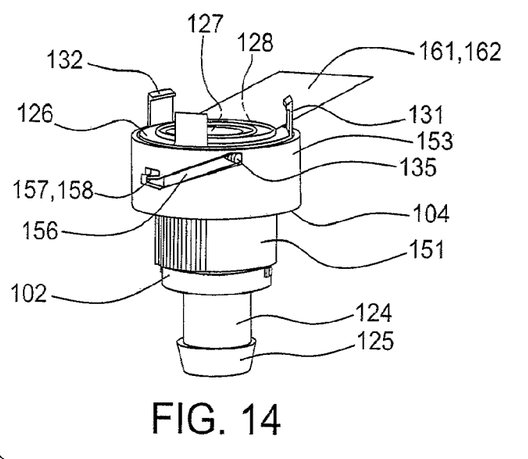
FIG. 14 is an isometric view of the male connector body, the moveable actuator, and the seal layer.

To enhance the sterility of the interiors of the female and male connector bodies, seal layers may be arranged to cover the openings at the first ends of the connector bodies. The seal layers may be variously configured. In the embodiments illustrated in FIGS. 13 and 14, each seal layer 161 may be configured as a peel strip removably attached to the first end 105 of the connector body 101, 102. The peel strip 161 may be joined to the face 116, 126 of the connector body 101, 102, sealingly covering the opening 117, 123 in the face 116, 126. For many embodiments the peel strip 161 may also cover all or at least a portion of the face seals 118, 127 without being joined to the face seals 118, 127. For example, each peel strip 161 may completely cover at least the innermost face seal 118, 127 closest to the opening 117, 123. The peel strip 161 may not be joined to the face seals 118, 127 themselves but may be joined to the surface of the face 116, 126 surrounding each face seal 118, 127. For many embodiments, the peel strip 161 is also not joined to any portion of the connector body 101, 102 radially inside the innermost face seal 118, 127. At least a portion of the peel strip 161 may be joined to the face 116, 126 in any manner that protects the sterility of the interior of the connector bodies 101, 102 and allows the peel strip 161 to be peeled off of the face 116, 126. For example, the peel strip 161 may be removably bonded or heat staked to the face 116, 126 of the connector bodies 101, 102. For embodiments that include face seals on only one of the female and male connector bodies, a sealing layer, e.g., a peel strip, may be attached to the face of the connector body without the face seals, covering the opening in the face. The peel strip 161 may also include an elongated pull tab 162. The tab 162 may be attached to the portion of the peel strip 161 that is joined to the face 116, 126 of the connector body 101, 102 by a fold 163. The tab 162 may fold back over the joined portion of the peel strip 161 and extend past the edge of the flange 115, 122 of the connector bodies 101, 102.

Figure 15:
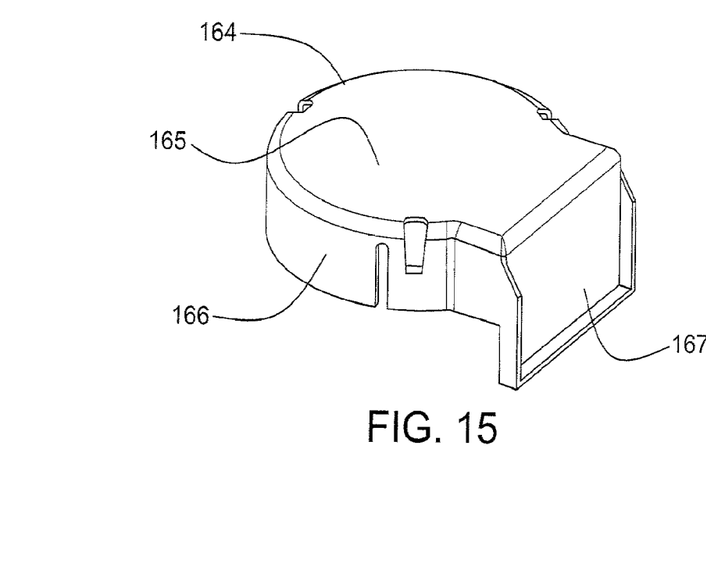
FIG. 15 is an isometric view of a cap for the female connector body.
Figure 16:
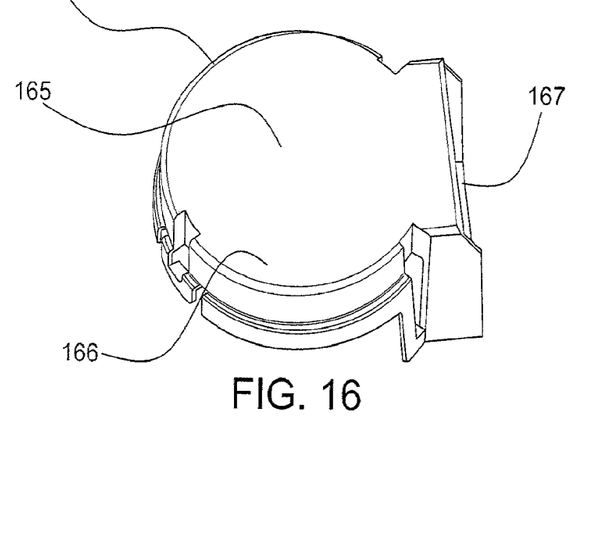
FIG. 16 is an isometric view of a cap for the male connector body.

To prevent inadvertent removal of or damage to the seal layer, each connector body may also include a removable cap which covers at least a substantial portion of the seal layer and the first end of the connector body. The cap can be fitted to the connector body at the first end, for example, by a friction fit or a snap fit, and may have any of a wide variety of configurations. For example, as shown in FIGS. 15 and 16 each cap 164 may have a rigid top 165 which protects the seal layer 161 and a skirt 166 which fits along the flange 115, 122 of the connector body 101, 102. The cap 164 may also include handle 167 which extends axially below the skirt 166. The pull tab 162 of the seal layer 161 may be bent axially under the handle 167, and the handle 167 may extend along all or at least a portion of the tab 162. The handle 167 may be used to lift the cap 164 off of the connector body 101, 102 and may also prevent inadvertent manipulation of the pull tab 162. The cap may also be configured to fit onto the male connector body in a manner that prevents inadvertent actuation of the actuator, for example, during packaging or shipping. For example, the cap may be fitted to the male connector body to about and lock the actuator in the initial position.

The components of the connector assembly may be formed from a wide variety of materials. For example, one or more of the connector bodies, the coupling mechanism, the piston, the moveable actuator and the caps may be made from any metallic material and/or polymeric material which is compatible with the fluid that will flow through the connector assembly. The metallic material may include, but is not limited to, a stainless steel. The polymeric material may include, but is not limited to, one or more of a polycarbonate, polypropylene, polyvinyl chloride, polyethersulphone, polyvinylidene fluoride, or polysulphone. For many embodiments a transparent or translucent polymeric material may be selected. The seal layer may be made from an impermeable material or a permeable material that resists the passage of contaminants, including biological containments. These materials include, but are not limited to, elastomeric sheets, polymeric films, and metal foils, e.g., aluminum foil, any of which may further include a reinforcing material. Further, the seal layer may be coated and/or impregnated with a biocide.

The components may be fabricated in a variety of ways, including molding, machining, pressing, and stamping, and may be fashioned into subassemblies. For example, the piston 103 may be inserted in the male connector body 102 before the fitting section 124 is mounted to the barrel section 121. The piston posts 148 may then be attached to the piston 103 by inserting the posts 148 through the side openings 136 in the male body 102 into the recesses 147 in the exterior of the piston 103. The moveable actuator 104 may then be slid onto the barrel section 121 with the collar 153 covering the piston posts 148, and the pins 135 of the male body 102 may be located in the initial position of the slots 156 in the moveable actuator 104. The fitting section 124 may then be attached to the barrel section 121, for example, by bonding or welding. The seal layer 161 may then be joined to the face 125 of the male connector body 102 to form a male connector subassembly. Another seal layer 161 may be joined to the face 116 of the female connector body 101 to form a female connector subassembly. Further, the female and male caps 164 may be mounted to the first ends 105 of the female and male connector subassemblies over the respective seal layers 161.

The subassemblies including the female and male connector bodies may be connected according to a variety of processes. The caps 164 may be removed from the subassemblies, exposing the sealing layers 161. For some embodiments, the seal layers may be removed prior to coupling the female and male connector bodies. However, to better protect the interior of the connector assembly from contamination, for many embodiments the seal layers 161 may remain on the connector bodies 101, 102 covering the face seals 118, 127 and the openings 117, 127 as the connector bodies 101, 102 are coupled to one another. The seal layers 161 may then be removed after the female and male connector bodies 101, 102 are coupled. For example, the seal layers 161 may be removed just before the moveable actuator 104 is moved from the initial position toward the actuated position.

The female and male connector bodies may be coupled in a variety of ways, including, for example, in accordance with the type of coupling mechanism. The connector bodies may be threaded, clamped, or ratcheted to one another if the coupling mechanism has threads, clamps or ratchets. In the illustrated embodiment, the female and male connector bodies 101, 102 may be snap-fitted to one another. For example, the first ends 105 of the connector bodies 101, 102 may be moved coaxially toward one another with the moveable piston 103 and actuator 104 in their initial positions. The arms 131 of the coupling mechanism 107 may engage and slide along the guide surfaces 134. The arms 131 and the guide surfaces 134 may be angularly spaced around the flanges 115, 122 of the connector bodies 101, 102 to provide only one angular orientation of the connector bodies 101, 102 that allows the connector bodies 101, 102 to be coupled, e.g., that allows the arms 131 to enter the guide surfaces 134. The seal layers 161 may be arranged on the first ends 105 such that in this angular orientation of the connector bodies 101, 102, the pull tabs 162 of the seal layers 161 overlie one another and extend in the same radial direction. Alternatively, the pull tabs may extend radially at an angle to one another, even in opposite directions.

Coupling the female and male connector bodies may also include sealing the face seal(s) of one connector body against the other connector body. For embodiments with the face seal(s) on the face of only one of the female and male connector bodies, sealing the face seal(s) may include pressing the face seal(s) of one connector body against the face of the other connector body, either directly or with the seal layers 161 between the face seal(s) and the opposing face. For embodiments with face seals 118, 127 on the faces 116, 126 of both the female and male connector bodies 101 102, sealing the face seals 118, 127 may pressing the face seals 118, 127 of the connector bodies 101, 102 against one another, either directly or with the seal layers 161 between the seals 118, 127. The face seals 118 of the female body 101 may lie on the same axis and have a similar diameter to the face seals 127 of the male body 102. As the connector bodies 101, 102 move closer to one another, the face seals 118, 127 may compress one another and may press the seal layers 161 against one another. When the female and male bodies 101, 102 are fully connected, the catches 132 of the coupling mechanism 107 may extend axially beyond the guide surfaces 134. The arms 131 and the catches 132 may then snap radially inwardly and the catches 132 may grasp the ledges 133, holding the female and male connector bodies 101, 102 together with the interiors of the connector bodies 101, 102 coaxially aligned at the openings 117, 123 in the flanges 115, 122 and the faces 116, 126 of the flanges 115, 122 closely positioned next to one another.

After the connector bodies 101, 102 are coupled, the seal layers 161 may be removed. For example, the pull tabs 162 may be pulled radially in a direction away from the connector bodies 101, 102. The portion of each seal layer 161 joined to the face 116, 126 of the flange 115, 122 may then peel off the face 116, 126, starting at the fold 163 and continuing diametrically across the face 116, 126 until the seal layer 161 is completely removed. As the seal layers 161 are removed from the faces 116, 126, any contaminants on the exposed portions of the seal layers 161 are removed along with the seal layers 161. Further, as the seal layers are peeled off of the faces, the seals on the faces expand and seal against one another. For example, as the seal layers 161 are peeled past a portion of the face seals 118, 127, that portion of each face seal 118, 127 immediately expands axially and directly contacts the expanding portion of the opposing face seal 127, 118. For embodiments having a face seal on only one face, the face seal expands against the opposing face as the seal layers are removed. With the face seal sealed against the opposing face or with the face seals 118, 127 sealed directly against one another, the interiors of the connector bodies 101, 102 fluidly communicate with one another through the coaxially aligned openings 117, 123 in the flanges 115, 122 in a sterile manner free of any external contamination.

After the seal layers are removed, the actuator may be moved from the initial position to the actuated position and, in response to movement of the actuator, the piston may be moved from the initial position to the engaged position. For example, for many embodiments the piston 103 in its initial position may be completely contained in the male connector body 102. The piston 103 may be located in the interior of the male body 102 with the first and second ends 141, 142 of the piston 103 between the first and second ends 105, 106 of the male body 102. The seal 145 near the first end 141 of the piston 103 may be sealed against the wall of the flange 122 at the opening 123 in the flange 122. The seal 146 near the second end 142 of the piston 103 may be sealed against the interior of the barrel section 121. Further, in the initial position of the piston 103, the piston posts 148 may be located near or contacting the second ends 138 of the side openings 136 in the male connector body 102. The actuator may be located on the exterior of the male connector body in the initial position. For example, the sleeve 151 may be located around the male body 102, e.g., around the barrel section 121, with the first end 152 of the sleeve 151 near or contacting the piston posts 148. The collar 153 may be located around the exterior of the male body 102, e.g., around the outer edge of the flange 122 and a portion of the barrel section 121. The pins 135 of the male body 102 may be located in the initial positions in the helical slots 156 in the actuator 104.

Moving the actuator to the actuated position may include rotating or twisting the actuator, and textural features, such as ribs, may be formed on the exterior of the actuator, e.g., the sleeve, to facilitate the rotational or twisting movement. Rotating the actuator may reduce the forces associated with actuating the connector assembly, including moving the actuator and the piston into the actuated and engaged positions. For example, the actuator 104 may be rotated to move the pins 135 relative to the helical slots 156 from the initial positions toward the actuated positions. Movement of the pins 135 toward the actuated positions in the helical slots 156 additionally drives the actuator 104, including the collar 153 and the sleeve 151, axially from the initial position toward the actuated position of the actuator 104. The actuator may then move axially along the exteriors of the male and female connector bodies. For example, the collar 153 may move axially along the outer edges of the flanges 122, 115 and the exterior surfaces of the arms 131 of the coupling mechanism 107, and the sleeve 151 may move axially toward the first end 105 of the male body 102.

In response to the movement of the actuator toward the actuated position, the piston moves toward the engaged position and at least a portion of the piston moves from the male connector body into the female connector body. For example, as the sleeve 151 moves toward the first end 105 of the male connector body 102, the first end 152 of the sleeve 151 contacts the piston posts 148 and drives the piston posts 148 along the side openings 136 in the male connector body 102 toward the first ends 137 of the side openings 136. If the side openings are oriented axially, the piston may move only axially within the male body. In the illustrated embodiment the side openings 136 may be oriented at an angle to the axis of the male body 102. As the posts 148 move along the angled side openings 136, a rotational or twisting movement in addition to an axial movement is imparted to the piston 103 by the posts 148. This rotational movement helps loosen the fictional engagement of the seals 145, 146 of the piston 103 against the interior of the male body 102, facilitating movement of the piston 103 from the initial position toward the engaged position. For embodiments in which the piston 103 is completely contained initially in the male connector body 102, the piston 103 may be mechanically isolated from the connections to the piping or tubing of the fluid system. Consequently, axial and/or rotational movement of the piston 103 does not exert any harmful forces on the piping or tubing, ensuring the integrity of the connections. As the piston 103 is driven by the posts from the initial position, the first end 141 of the piston 103 may exit the male connector body 102 through the opening 123 in the male flange 122 and enter the female body 101 through the opening 117 in the female flange 115. The seal 145 near the first end 141 of the piston 103 may move at least axially along the wall defining the opening 123 of the male flange 122 and axially along the interior of the guide section 112 of the female connector body 101, maintaining a seal along the distance that it travels. The seal 146 near the second end 142 of the piston 103 may move at least axially along the male connector body 102, e.g., along the barrel section 121, maintaining a seal along the distance that it travels.

In response to moving the actuator into the actuated position, the piston may be moved to the engaged position. For example, rotating the actuator 104 to the actuated position moves the pins 135 into the actuated positions in the helical slots 156, which moves the actuator 104, including the sleeve 151, axially. Moving the first end 152 of the sleeve 151 to the actuated position drives the posts 148 toward the first ends 137 of the side openings 136, which limit further movement of the posts 148, and drives the piston 103 to the engaged position. In the engaged position, the piston 103 bridges the female and male connector bodies 101, 102; the first end 141 of the piston 103 is located between the first and second ends 105, 106 of the female connector body 101, while the second end 142 of the piston 103 is located between the first and second ends 105,106 of the male connector body 102; and the seal 145 near the first end 141 of the piston 103 seals against the interior of the female connector body 101, e.g., against the interior of the guide section 112, while the seal 146 near the second end 142 of the piston 103 seals against the interior of the male connector body 102, e.g., against the interior of the barrel section 121. The interior of the piston 103 then fluidly communicates between the second ends 106 of the female and male connector bodies 101, 102.

Moving the actuator to the actuating position may include locking the actuator in place in the actuating position, which, in turn, may also include locking the coupling mechanism in place joining the female and male connector bodies and/or locking the piston in the engaged position bridging the female and male connector bodies. For example, rotation of the actuator 104 may move the pins 135 over the clip 158 of the locking mechanism 157 into the actuated positions in the helical sots 156, where the pins 135 may be locked in place by the locking mechanism 157, e.g., by the clip 158. Locking the pins 135 in the actuated positions of the slots 156 locks the actuator 104, including the collar 153 and the sleeve 151, in the actuated position. The collar 153 may be locked in place around the coupling mechanism 107, for example, around and closely adjacent to the exteriors of the arms 131, which prevents the arms 131 from bending radially outwardly and disengaging the catches 132 from the ledges 133. The sleeve 151 may be locked in place against the piston posts 148, which prevents the piston 103 from moving out of the engaged position.

After the connector bodies 101, 102 are coupled, any peel strips 161 are removed, and the actuator 104 and piston 103 are moved to their actuated/engaged positions, fluid is free to flow through the connector assembly 100. For example, fluid may flow into the second end 106 of either the female or male connector body 101, 102, through the interior of the connector body 101, 102, through the interior of the hollow piston 103 bridging the connector bodies 101, 102, through the interior of the other connector body 102, 101, and out of the second end 106 of the other connector body 102, 101. External contamination, which was initially prevented from entering the connector bodies 101, 102 by the seal layers 161, is prevented from entering the connector assembly 100 and contaminating the fluid by the seal(s) 118, 127 at the faces 116, 126 of the connector bodies 101, 102 and the seals 145, 146 between the piston 103 and the interior of the connector bodies 101, 102, providing a highly sterile connection. Further, because the seals 145, 146 between the piston 103 and the connector bodies 101, 102 may be shaft seals, the connector assembly, including the female and male connector bodies 101, 102 and the piston 103, are capable of accommodating larger flows and higher pressures, e.g., up to about 3 bar or more, allowing larger internal diameters, e.g., up to about 2.5 cm or more, for the piston 103 and the connector bodies 101, 102.

Although the invention has been disclosed by the embodiments previously described and illustrated, the invention is not limited to those embodiments. For instance, one or more features of an embodiment may be eliminated or modified, one or more features of any embodiment may be combined with one or more features of other embodiments, or embodiments with very different features may be envisioned without departing from the scope of the invention. For example, for some embodiments the seal layer may be eliminated and a tighter fitting cap may protect against external contaminants. For other embodiments the seal layer may comprise a more permanently mounted seal layer in addition to, or instead of, the removable peel strip. The piston may then include a piecing element on its first end which pierces the permanent seal layer when the actuator moves the piston toward its engaged position. For some embodiments, the sleeve may be eliminated and the flange of the collar may contact and drive the piston posts toward the engaged position. For other embodiments, the collar may be eliminated and the pin-in-slot arrangement may, for example, be associated with the barrel section and the sleeve. For some embodiments the actuator may move only axially and not rotate. For example, the actuator may comprise an axial slide coupled to the piston instead of a rotatable sleeve or collar. For other embodiments the actuator may only rotate and not move axially. For example, the actuator may be mechanically coupled to the piston by a pin-in-helical-slot arrangement which drives the piston axially as the actuator rotates. For some embodiments the female and/or male connector bodies may additionally serve as a housing containing an element such as a sensor, a valve, or a filter. For example, the element may be mounted within the fitting section 113, 124 or the barrel section 111, 121 in a manner that does not interfere or restrict the movement of the piston 103.

Figure 17:
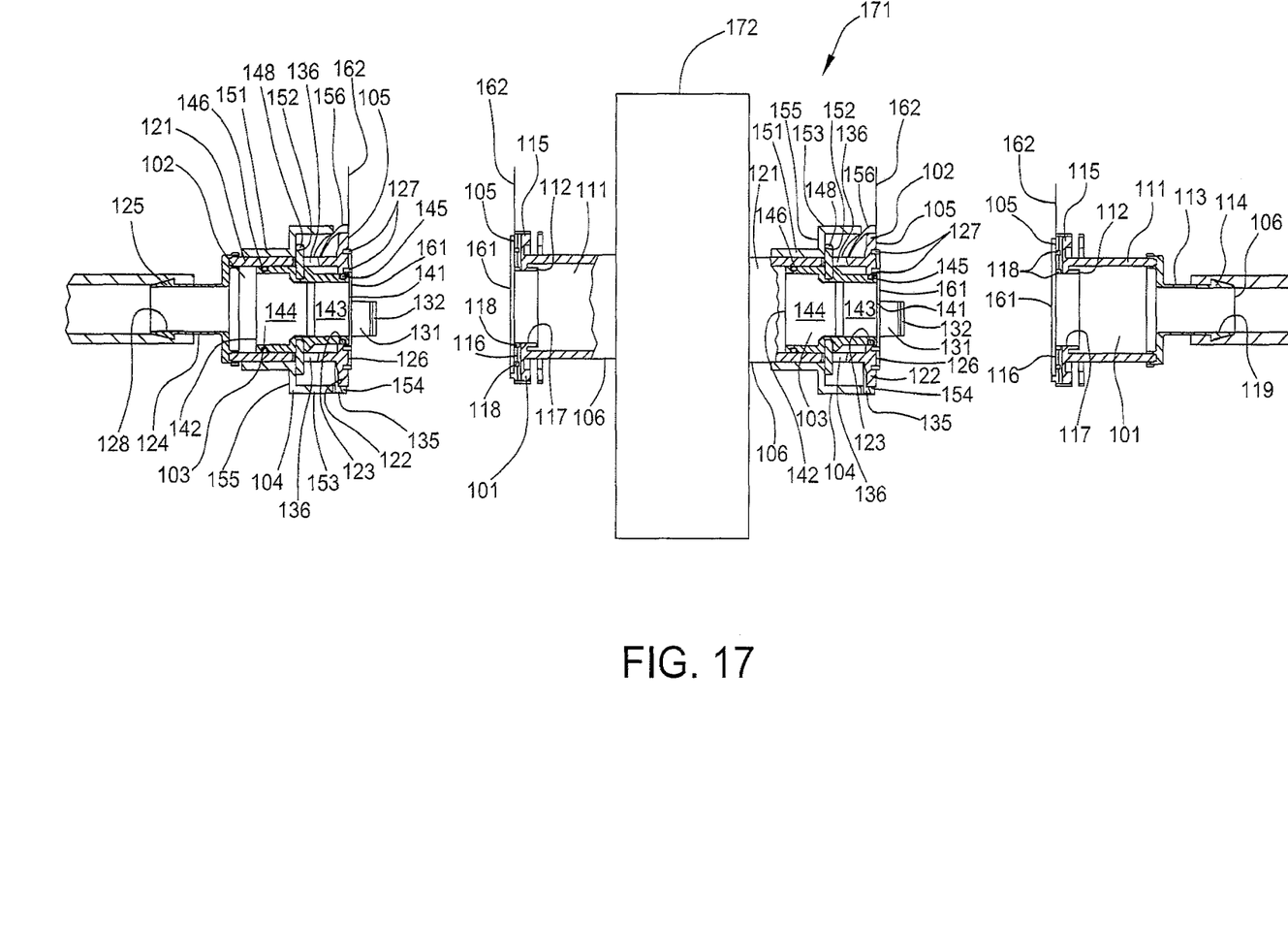
FIG. 17 is a view of a device including connector subassemblies.

For some embodiments, one or both of the female and male connector subassemblies may be integrally connected to, including integrally formed with, another component instead of being connected to a pipe, tube or other conduit. The component may include a flexible or rigid container, for example, a bag, a vessel, or a housing which may contain another element of the component, such as a sensor, a valve, or a filter. For example, the female and/or male connector subassemblies may be integrally connected to a component and may serve as an inlet and/or an outlet for the component. One of many different examples of these embodiments is the device 171 shown in FIG. 17. The device 171 may include a housing 172 which may serve as a container for any of numerous elements, including, for example, a filter (not shown). The female connector subassembly, including the female connector body 101 and the seal layer 161, may serve as the inlet, while the male connector subassembly, including the male connector body 102, the piston (not shown), the actuator 104, and the seal layer 161, may serve as the outlet, or vice versa. Alternatively, both the inlet and the outlet may comprise female connector subassemblies or both may comprise male connector subassemblies. Further, for some embodiments the component may have only one connector subassembly which serves to supply fluid to the container of the component or withdraw fluid from the container of the component.

The connector bodies may be integrally connected to the container, e.g., the housing of the device, in any of numerous locations on the housing. For example, one or both connector bodies may be integrally connected on the top, bottom, and/or side of the housing. In the illustrated embodiment, the second ends 106 of the connector bodies 101, 102 may be integrally connected to the opposite ends of the housing 172. Further, the connector subassemblies, including the connector bodies, the piston, the actuator, the seal layers, and the caps, may have any of numerous configurations which allow the connector subassembly to be integrally connected to the component. For example, both of the female and male connector subassemblies which are integrally connected to the housing 172 of the device 171 shown in FIG. 17 may be identical to any of the subassemblies previously described. (Aspects of the connector subassemblies shown in FIG. 17 which are identical to those of the previously described connector assemblies have the same reference numerals.). However, the fitting sections of the connector bodies 101, 102 may be omitted. Instead, the barrel sections 111, 121 of the connector bodies 101, 102 may be integrally connected at the second end 106 to the housing 172, for example, by a bond or a weld. Alternatively, the fitting sections may remain but may be configured to be integrally connected to the housing, for example, by a threaded or clamp connection.

The container of the component may define a fluid flow path through the container from the inlet connector subassembly to the outlet connector subassembly, and the element within the container may be positioned in the fluid flow path, e.g., across the fluid flow path. For example, the housing 172 of the device 171 may define a fluid flow path through the housing 172 between the female connector subassembly 101 and the male connector subassembly 102. The filter may be positioned within the housing 172 across the fluid flow path.

To connect the component to the fluid system, each female or male connector subassembly integrally connected to the component may be coupled to a male or female subassembly of another device or conduit of a fluid system in the any of ways previously described. For example, the female connector subassembly of the device 171 may be connected to a male connector subassembly of the fluid system by coupling the female connector body 101 of the device 171 to the male connector body of the fluid system, removing the peel strips 161, and moving the actuator on the male connector body to the actuated position, which moves the piston in the male connector body into the engaged position in the female connector body 101 of the device 171. Similarly, the male connector subassembly of the device 171 may be connected to a female connector subassembly of the fluid system by coupling the male connector body 102 of the device 171 to the female connector body of the fluid system, removing the peel strips 161, and moving the actuator 104 on the male connector body 102 to the actuated position, which moves the piston in the male connector body 102 into the engaged position in the female connector body of the fluid system. Fluid flow may then be established in either direction through the component, e.g., through the device 171, via the fluid system.

The present invention thus encompasses innumerable embodiments and is not restricted to the particular embodiments that have been described and/or illustrated herein. Rather, the present invention includes all embodiments and modifications that may fall within the scope of the claims.

The invention claimed is:

1. A connector assembly for making fluid connections comprising:

a first hollow connector body and a second hollow connector body, each body having first and second ends, an exterior, and an interior which extends between the first and second ends;

a coupling mechanism arranged to couple the first and second connector bodies at the first ends of the bodies;

a hollow piston having first and second ends, an interior extending between the first and second ends, an exterior, and first and second seals on the exterior of the piston, the piston being moveable from a first position, wherein the piston is positioned in the interior of the first connector body and the first and second seals seal against the interior of the first connector body, to a second position, wherein the piston extends between the first and second connector bodies and the first and second seals seal against the first and second connector bodies, respectively; and a moveable actuator, the actuator being axially moveable from a first position, wherein the actuator is located on the exterior of the first connector body, to a second position, wherein the actuator is located around the coupling mechanism, the actuator and the piston being coupled to move the piston from the first position to the second position in response to movement of the actuator from the first position to the second position.

2. The connector assembly of claim 1 wherein the first connector body has at least one side opening and wherein the actuator is mechanically coupled through the side opening in the first connector body to the piston between the first and second piston seals.

3. The connector assembly of claim 1 wherein the actuator and the piston are mechanically coupled without being integrally connected.

4. The connector assembly of claim 1 wherein the piston includes a protrusion and wherein the actuator is arranged to abut the protrusion without being integrally connected to the protrusion.

5. The connector assembly of claim 1 wherein the coupling mechanism comprises a snap-fit arrangement including at least one bendable arm extending between the first and second connector bodies and wherein the moveable actuator is axially spaced from the bendable arm in the first position of the actuator and is positioned along the exterior of the bendable arm in the second position to prevent the arm from bending.

6. The connector assembly of claim 1 wherein in the first position the first and second ends of the piston are located between the first and second ends of the first connector body and wherein in the second position the first end of the piston is located between the first and second ends of the second connector body and the second end of the piston is located between the first and second ends of the first connector body, the interior of the piston fluidly communicating between the second ends of the first and second connector bodies.

7. The connector assembly of claim 1 further comprising a seal layer positioned along the first end of at least one of the first and second connector bodies.

8. The connector assembly of claim 1 wherein the seal layer comprises a removable peel strip.

9. The connector assembly of claim 1 wherein at least one of the first and second connector bodies includes a seal located at the first end of the connector body and arranged to seal against the other connector body at the first end.

10. The connector assembly of claim 1 wherein each connector body includes a seal located at the first end of the connector body and arranged to seal against the seal of the other connector body.

11. A connector assembly for making fluid connections comprising:
a first hollow connector body and a second hollow connector body, each body having first and second ends, an exterior and an interior which extends between the first and second ends;
a coupling mechanism arranged to couple the first and second connector bodies at the first ends of the bodies;
a hollow piston having first and second ends, an interior and an exterior extending between the first and second ends, and first and second seals on the exterior of the piston, the piston being movable from a first position, wherein the piston is movably located in the interior of the first connector body, the first and second ends of the piston are located between the first and second ends of the first connector body, and the first and second seals are sealed to the first connector body, to a second position, wherein the piston bridges and seals against the interiors of the first and second connector bodies, the first end of the piston is located between the first and second ends of the second connector body and the second end of the piston is located between the first and second ends of the first connector body, and the first and second seals seal against the first and second connector bodies, respectively, the interior of the piston fluidly communicating between the second ends of the first and second connector bodies; and a rotatable actuator mounted around the exterior of at least one of the first and second connector bodies and coupled to the piston to move the piston from the first position to the second position in response to rotation of the actuator.

12. The connector assembly of claim 11 wherein the piston has an exterior and first and second seals on the exterior of the piston.

13. The connector assembly of claim 11 wherein the actuator and the piston are mechanically coupled without being integrally connected.

14. The connector assembly of claim 11 wherein the rotatable actuator is axially moveable from a first position, wherein the actuator is axially spaced from the coupling mechanism, to a second position, wherein the actuator is located around the coupling mechanism, the actuator and the piston being mechanically coupled to move the piston from the first position to the second position in response to movement of the actuator from the first position to the second position.

15. The connector assembly of claim 11 wherein each connector body has an opening at the first end communicating with the interior of the connector body, wherein at least one of the first and second connector bodies includes a seal surrounding the opening, and wherein the connector assembly includes a removable peel strip extending along the first end of each connector body and covering the opening to seal the interior of the connector body from exterior contaminants.

16. A process for making fluid connections comprising:
coupling first and second hollow connector bodies at first ends of the bodies by a coupling mechanism;
moving an actuator from a first position, wherein the actuator is located on an exterior of the first connector body, to a second position, wherein the actuator is located around the coupling mechanism; and
in response to movement of the actuator, moving a hollow piston coupled to the actuator from a first position, wherein the piston is positioned in an interior of the first connector body and first and second seals on the exterior of the piston are sealed to the first connector body, to a second position, wherein the piston extends between the first and second connector bodies and the first and second seals are sealed to the first and second connector bodies, respectively.

17. The process of claim 16 further comprising removing peel strips from the first ends of the first and second connector bodies after coupling the first and second connector bodies.

18. The process of claim 16 wherein moving the actuator includes rotating the actuator.

19. A process for making fluid connections comprising:
coupling first and second hollow connector bodies at first ends of the bodies;

rotating an actuator around an exterior of at least one of the first and second connector bodies; and in response to rotating the actuator, moving a hollow piston coupled to the actuator from a first position, wherein the piston is slideably located in the interior of the first connector body, first and second ends of the piston are located between first and second ends of the first connector body, and first and second seals on the exterior of the piston seal against the first connector body, to a second position, wherein the piston bridges and seals against interiors of the first and second connector bodies, the first end of the piston is located between the first and second ends of the second connector body and the second end of the piston is located between first and second ends of the first connector body, the first and second seals seal against the first and second connector bodies, respectively, and the interior of the piston fluidly communicates between the second ends of the first and second connector bodies.

20. The process of claim 19 further comprising removing peel strips from the first ends of the first and second connector bodies after coupling the first and second bodies.

21. A fluid system comprising a conduit and the connector assembly of claim 1, wherein the conduit is connected to one of the first and second connector bodies.

22. A fluid system comprising a component and the connector assembly of claim 1, wherein the component includes a container and one of the first and second connector bodies is integrally connected to the container.

23. A fluid system comprising a conduit and the connector assembly of claim 11, wherein the conduit is connected to one of the first and second connector bodies.

24. A fluid system comprising a component and the connector assembly of claim 11, wherein the component includes a container and one of the first and second connector bodies is integrally connected to the container.

25. The connector assembly of claim 12 wherein the first connector body has at least one side opening and wherein the actuator is mechanically coupled through the side opening on the first connector body to the piston between the first and second piston seals.

* * * * *